United States Patent [19]

Ong

[11] Patent Number: 5,270,286
[45] Date of Patent: Dec. 14, 1993

[54] HERBICIDAL EMULSIFIABLE CONCENTRATE COMPOSITIONS OF IMIDAZOLINONE HERBICIDES

[75] Inventor: Chungjian J. Ong, Warren, N.J.

[73] Assignee: American Cyanamid Company, Wayne, N.J.

[21] Appl. No.: 648,083

[22] Filed: Jan. 31, 1991

[51] Int. Cl.⁵ .................. A01N 33/18; A01N 43/50; A01N 43/42
[52] U.S. Cl. ...................... 504/130; 504/148; 504/116
[58] Field of Search .............. 71/92, 121, DIG. 1; 504/116, 130, 148

[56] References Cited

U.S. PATENT DOCUMENTS

| | | | |
|---|---|---|---|
| 4,165,231 | 8/1979 | Lutz et al. | 71/121 |
| 4,647,301 | 3/1987 | Los | 71/92 |
| 4,749,404 | 6/1988 | Parsons | 71/92 |
| 4,776,876 | 10/1988 | Nordhoff et al. | 71/92 |
| 4,822,405 | 4/1989 | Martin et al. | 71/92 |
| 4,871,388 | 10/1989 | Pasarela et al. | 71/92 |
| 4,923,504 | 5/1990 | Los | 71/92 |

*Primary Examiner*—Richard L. Raymond
*Assistant Examiner*—B. Bembenick
*Attorney, Agent, or Firm*—John W. Hogan, Jr.

[57] ABSTRACT

The present invention provides herbicidal emulsifiable concentrate compositions of imidazolinone herbicides and dinitroaniline herbicides.

7 Claims, No Drawings

HERBICIDAL EMULSIFIABLE CONCENTRATE COMPOSITIONS OF IMIDAZOLINONE HERBICIDES

BACKGROUND OF THE INVENTION

U.S. Pat. No. 4,749,404 describes herbicidal liquid concentrate compositions of salts of 2-(4-isopropyl-4-methyl-5-oxo-2-imidazolin-2-yl)-3-quinolinecarboxylic acid which may be combined with an organic dinitroaniline composition and U.S. Pat. No. 4,822,405 describes concentrated oil in water emulsion combination compositions of water soluble salts of imidazolinone herbicides and dinitroaniline herbicides. However, the ratio of herbicides which may be employed is limited because of problems with crystallization which may occur with more concentrated formulations especially when storing the compositions at low temperatures. In addition, these compositions employ salts of imidazolinones and require both aqueous and organic solvents.

Pending application for U.S. Letters, Patent Ser. No. 440,179, filed on Nov. 22, 1989 (abandoned) describes herbicidal emulsifiable suspension concentrate compositions which contain an active herbicidal agent or combination of agents. However, suspension compositions are not entirely satisfactory because crystallization of the active herbicidal agent, upon extended storage at low temperature, is enhanced by the solid active herbicide present in the suspension.

It is therefore an object of the present invention to advantageously provide an emulsifiable concentrate combination composition in which all of the active herbicidal agents are dissolved in a single solvent which may be stored at lower temperatures and for a longer period of time than suspension concentrate compositions or concentrated oil in water emulsion compositions.

It is also an object of the present invention to provide herbicidal emulsifiable concentrate compositions of free acids of imidazolinone herbicides and 2,6-dinitroaniline herbicides which are physically and chemically stable.

SLTMMARY OF THE INVENTION

The present invention relates to a herbicidal emulsifiable concentrate composition which comprises 0.5% to 5% by weight of an imidazolinyl acid; 0% to about 40% by weight of a 2,6-dinitroaniline derivative; 2% to 6% of an alkylarylsulfonic acid; ethylene oxide/propylene oxide block copolymer and alkylphenol polyethylene oxide condensate emulsifying agents; an antigelation agent; and an aromatic solvent.

DETAILED DESCRIPTION OF THE INVENTION

A preferred embodiment of the invention is herbicidal emulsifiable concentrate compositions comprising on a weight basis about 0.5% to 5% of an imidazolinyl acid represented by structural formula I

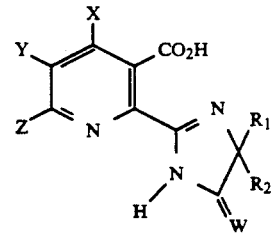

wherein
W is oxygen or sulfur;
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
X is hydrogen, halogen, hydroxyl or methyl;
Y and Z are independently hydrogen, halogen, $C_1$–$C_6$ alkyl, $C_1$–$C_4$ alkoxyalkyl, hydroxloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino, or $C_1$–$C_4$ alkylsulfonyl group or phenyl optionally substituted with one $C_1$–$C_4$alkyl, $C_1$–$C_4$alkoxy or halogen; and when taken together, Y and Z may form a ring in which YZ are represented by the structure: —$(CH_2)_n$—, where n is an integer of 3 or 4, provided that X is hydrogen; or

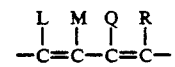

where L, M, Q and R are independently hydrogen, halogen, $C_1$–$C_4$ alkyl or $C_1$–$C_4$ alkoxy;
0% to about 40% of a herbicidal 2,6-dinitroaniline derivative represented by structural formula II

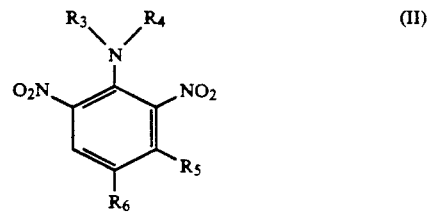

wherein
$R_3$ is hydrogen, $C_2$–$C_4$ alkyl or chloroethyl;
$R_4$ is $c_2$–$C_5$ alkyl, chloroethyl, 2-methallyl or cyclopropylmethyl;
$R_5$ is hydrogen, methyl or amino;
$R_6$ is trifluoromethyl, $C_1$–$C_3$ alkyl, -$SO_2NH_2$ or $SO_2CH_3$;
2% to 6% of an alkylarylsulfonic acid; 2% to 6% of an ethylene oxide/propylene oxide block copolymer; 1% to 6% of an alkylphenol polyethylene oxide condensate; 0.5% to 10% of an antigelation agent and a sufficient amount of an aromatic solvent to total 100%.

A most preferred embodiment of the present invention comprises on a weight basis 0.5% to 5% of a formula I imidazolinyl acid, 20% to 40% of a formula II 2,6-dinitroaniline derivative, 2% to 6% of an alkylarylsulfonic acid, 2% to 6% of an ethylene oxide/propylene oxide block copolymer, 1% to 6% of an alkylphenol polyethylene oxide condensate, 0.5% to 10% of an antigelation agent and a sufficient amount of an aromatic solvent to total 100%.

Surprisingly, it has been found that the compositions of the present invention provide physically and chemically stable herbicidal emulsifiable concentrate compositions of formula (I) imidazolinyl acids and formula (II) 2,6-dinitroaniline derivatives which remain free-flowing and homogeneous for extended periods of time, and also remain physically and chemically stable after repeated freezing and thawing cycles without precipitating insoluble solids.

The alkyarylsulfonic acid of the present invention is an especially important element of the present compositions and should be present in at least an amount equal to about 1.2 times the percent by weight of the imidazolinyl acid to ensure that the acid completely dissolves in the aromatic solvent. Alkylarylsulfonic acids suitable for use in the compositions of the invention include $C_8$–$C_{18}$ alkylbenzenesulfonic acids, with dodecylbenzenesulfonic acid being most preferred.

Antigelation agents are used in the compositions of the present invention to ensure that the compositions remain homogeneous and free-flowing. Antigelation agents which are suitable for use in the compositions of the present invention include N-methylpyrrolidone, cyclohexanone, alcohols such as ethanol and methanol, glycols such as propylene glycol and ethylene glycol and the like with N-methylpyrrolidone being most preferred.

A preferred group of ethylene oxide/propylene oxide block copolymers suitable for use in the compositions of the present invention are butyl-omega-hydroxypoly(oxypropylene)block polymer with poly(oxyethylene) having an average molecular weight in a range of 2,400 to 3,500, with alpha-butyl-omega-hydroxy-ethylene oxide-propylene oxide block copolymers having an HLB of 12 and a viscosity at 25°0 C. of 2,000 CPS, (TOXIMULO ® 8320, Stepan Chemical Co.) being a most preferred member of this class of emulsifiers.

Preferred alkylphenol polyethylene oxide condensates suitable for use in the compositions of the present invention are the nonylphenol ethoxylates, with nonylphenol ethoxylate (9 to 10 mols of ethylene oxide)(FLO MO ®89N, DeSoto, Inc., Sellers Chemical Div.) being a most preferred member of this class of emulsifiers.

Aromatic solvents suitable for use in the compositions of this invention include aromatic hydrocarbon and chlorinated aromatic hydrocarbon solvents and mixtures thereof; such as toluene, xylenes, polynuclear aromatic hydrocarbons such as naphthalenes and alkylnaphthalenes and mixtures thereof, many of which are available from the fractionation of crude oil and in general have distillation ranges in the temperature range of from about 140° C. to 305° C., with those having a distillation range of from about 183° to 280° C. being most preferred, and are commercially available under a variety of tradenames; and mono or polychlorobenzene and toluenes.

Imidazolinyl acids particularly useful in the compositions of the present invention are 2-(4-iso-propyl-4-methyl-5-oxo-2-imidazolin-2-yl)-3-quinoline-carboxylic acid, 5-ethyl-2-(4-isopropyl-4-methyl-5-oxo-2-imidazolin-2-yl)nicotinic acid, 2-(4-isopropyl-4-methyl-5-oxo-2-imidazolin-2-yl)nicotinic acid and 2-(4-isopropyl-4-methyl-5-oxo-2-imidazolin-2-yl)-5(methoxymethyl)-nicotinic acid.

2,6-Dinitroaniline derivatives which are especially suitable for use in the compositions of the present invention are pendimethalin and trifluralin.

The emulsifiable concentrate compositions of the present invention may conveniently be prepared by admixing the formula (I) imidazolinyl acid with a solution of the desired antigelation agent, alkylarylsulfonic acid, ethylene oxide/propylene oxide block copolymer, alkylphenol polyethylene oxide condensate and aromatic solvent until all of the solids are dissolved, then the formula (II) 2,6-dinitroaniline derivative is added to the solution and mixing is continued until a homogeneous solution is obtained.

The following examples are provided to further illustrate the compositions of the present invention but are not limitative of the invention described herein.

EXAMPLE 1

Preparation of herbicidal emulsifiable concentrate Compositions

Solid 5-ethyl-2-(4-isopropyl-4-methyl-5-oxo-2-imidazolin-2-yl)nicotinic acid (2.62g, 93.4 pure, 2.62% on a weight basis) is added to a stirred solution of N-methylpyrrolidone (4g, 4% on a weight basis) and dodecylbenzenesulfonic acid (4g, 4% on a weight basis). The mixture is stirred until all of the solids dissolve. An aromatic hydrocarbon mixture ($C_{10}$ to $C_{13}$) aromatics having a distillation range of from about 226°–279° C. (AROMATIC ® 200, Exxon)(45.68g, 45.68% on a weight basis) is added to the mixture and stirring is continued until a homogeneous solution of obtained. Pendimethalin (35.7g, 92.3% pure, 35.7% on a weight basis) is added to the homogeneous solution and stirring is continued until the solids dissolve. Next, nonylphenol ethoxylate (9 to 10 mols of ethylene oxide)(4g, 4% on a weight basis) and alpha-butyl-omega-hydroxy-ethylene oxide propylene oxide block copolymer having a HLB of 12 and a viscosity at 250° C. of 2,000 CPS (4g, 4% on a weight basis) are added to the mixture and stirring is continued until a homogeneous solution is obtained which is then filtered through 1.5 micron filter paper to obtain a clear dark brown solution having a density at 20° C. of 1.0683 g/mL.

Following the procedure of Example 1, but using the compounds listed in Table I below gives the emulsifiable concentrate compositions listed in Table II below.

TABLE I

| Herbicidal Imidazolinyl Acid | |
|---|---|
| a. | 5-ethyl-2-(4-isopropyl-4-methyl-5-oxo-2-imidazolin-2-yl)nicotinic acid |
| Herbicidal 2,6-Dinitroaniline Derivative | |
| b. | pendimethalin |
| c. | trifluralin |
| Alkylarylsulfonic Acid | |
| d. | dodecylbenzene sulfonic acid |
| Antigelation Agent | |
| e. | N-methylpyrrolidone |
| f. | cyclohexanone |
| g. | dipropylene glycol |
| Ethylene Oxide/propylene Oxide Block Copolymer | |
| h. | alpha-butyl-omega-hydroxy-ethylene oxide-propylene oxide block copolymer having an HLB of 12 and a viscosity at 25° C. of 2,000 CPS |
| Alkylphenol Polyethylene Oxide Condensate | |
| i. | nonylphenol ethoxylate (6 mols of ethylene oxide) |
| j | nonylphenol ethoxylate (9–10 mols of ethylene |

TABLE I-continued

| | |
|---|---|
| | oxide) |
| k. | nonylphenol ethoxylate (11 mols of ethylene oxide) |
| l. | nonylphenol ethoxylate (13 mols of ethylene oxide) |
| m. | nonylphenol ethoxylate (15 mols of ethylene oxide) |
| n. | nonylphenol ethoxylate (30 mols of ethylene oxide) |
| Aromatic Solvent | |
| o. | aromatic hydrocarbon mixture ($C_{10}$ to $C_{13}$ aromatics, distillation range 226°–279° C.) (AROMATIC ® 200, Exxon) |
| p. | aromatic hydrocarbon mixture ($C_9$ to $C_{12}$ aromatics, distillation range 183°–210° C.) (AROMATIC ® 150, Exxon) |

TABLE II

Emulsifiable Concentrte Compositions

| Composition | Imidazolinyl acid/ % W/W | 2,6-Dinitroaniline/ % W/W | Alkylarylsulfonic acid/ % W/W | Antigelation agent/ % W/W | Ethylene oxide/ propylene oxide block copolymer/ % W/W | Alkylphenol polyethylene oxide Condensate/% W/W | Aromatic Solvent/ % W/W |
|---|---|---|---|---|---|---|---|
| 1 | a/2.62 | b/35.70 | d/4.0 | e/4.0 | h/4.0 | j/4.0 | o/45.68 |
| 2 | a/2.40 | b/33.40 | d/4.0 | e/8.0 | h/4.0 | j/4.0 | o/44.20 |
| 3 | a/2.60 | b/35.80 | d/4.0 | e/8.0 | h/4.0 | j/2.0 | o/43.60 |
| 4 | a/2.40 | b/33.40 | d/4.0 | e/4.0 | h/4.0 | j/4.0 | o/48.20 |
| 5 | a/2.40 | b/33.40 | d/4.0 | e/4.0 | h/3.0 | j/4.0 | o/49.20 |
| 6 | a/2.40 | b/33.40 | d/4.0 | e/4.0 | h/2.0 | j/4.0 | o/50.20 |
| 7 | a/2.40 | b/33.40 | d/4.0 | e/4.0 | h/3.0 | j/3.0 | o/50.20 |
| 8 | a/2.40 | b/33.40 | d/4.0 | e/4.0 | h/2.0 | j/3.0 | o/51.20 |
| 9 | a/2.60 | b/35.80 | d/4.0 | e/0.5 | h/4.0 | j/4.0 | o/50.90 |
| 10 | a/2.60 | b/35.80 | d/4.0 | f/1.0 | h/4.0 | j/4.0 | o/48.60 |
| 11 | a/2.60 | b/35.80 | d/4.0 | g/1.0 | h/4.0 | j/4.0 | o/48.60 |
| 12 | a/2.60 | b/35.80 | d/4.0 | e/8.0 | h/4.0 | n/1.0 | o/44.60 |
| 13 | a/2.50 | b/34.60 | d/4.0 | e/1.0 | h/4.0 | n/1.0 | o/51.90 |
| 14 | a/2.65 | c/29.66 | d/3.0 | e/2.0 | h/3.0 | j/3.0 | p/56.69 |
| 15 | a/2.65 | c/29.66 | d/3.0 | e/4.0 | h/3.0 | j/3.0 | p/54.69 |
| 16 | a/2.45 | c/29.66 | d/3.0 | e/4.0 | h/3.0 | i/3.0 | p/54.89 |
| 17 | a/2.45 | c/29.66 | d/3.0 | e/4.0 | h/3.0 | k/3.0 | p/54.89 |
| 18 | a/2.45 | c/29.66 | d/3.0 | e/4.0 | h/3.0 | l/3.0 | p/54.89 |
| 19 | a/2.45 | c/29.66 | d/3.0 | e/4.0 | h/3.0 | m/3.0 | p/54.89 |
| 20 | a/2.62 | c/29.66 | d/4.0 | e/8.0 | h/4.0 | j/4.0 | p/47.72 |
| 21 | a/2.45 | c/29.44 | d/3.0 | e/4.0 | h/3.0 | j/3.0 | o/55.11 |

TABLE III

Low Temperature Experiments

| Composition | Crystallization Temperature °C. |
|---|---|
| Control | 13° C. |
| 2 | −1° C. |
| 4 | −3° C. |
| 9 | 0° C. |
| 11 | 0° C. |

EXAMPLE 2

Low temperature stability of emulsifiable concentrate compositions of the invention Two 10mL samples of compositions 2 and 4 prepared in the above example are placed in a constant temperature bath maintained at 5° C. and the temperature of the samples is allowed to equilibrate for two hours. Seeds of pendimethalin crystals and 5-ethyl-2-(4-isopropyl-4-methyl-5-oxo-2-imidazolin-2-yl)nicotinic acid powder are added to the samples. After 48 hours, the samples are visually inspected for evidence of crystallization. The temperature of the bath is then lowered in 1° C. increments holding the sample at each temperature for hours until crystallization is observed. A comparative control composition containing on a weight basis 34.00% pendimenthalin (93% real), 2.30% 5-ethyl-2-(4-isopropyl-4-methyl-5-oxo-2-imidazolin-2-yl)nicotine acid (98% water is also ammonium hydroxSde, 27.42% aromatip mixture (AROMATIC® 200, Exxon), 4.00% surfactants and 31.58% water is also evaluated similarly except the initial testing temperature is set at 15° C. instead of 5° C. The results of these experiments are summarized in Table III below.

What is claimed is:

1. A herbicidal emulsifiable concentrate composition which comprises 0.5% to 5% by weight of an imidazolinyl acid, about 20% to 40% by weight of a 2,6- dinitroaniline derivative; 2% to 6% by weight of an alkylarylsulfonic acid, with the proviso that the alkylarylsulfonic acid by present in at least an amount equal to about 1.2 times the percent by weight of the imidazolinyl acid; ethylene oxide/propylene oxide block copolymer and alkylphenol polyethylene oxide condensate emulsifying agents; and antigenlation agent and an aromatic solvent selected from the group consisting of aromatic hydrocarbon solvents, chlorinated aromatic hydrocarbon solvents, and mixtures thereof having a distillation range of from about 140° C. to 305° c., wherein the imidazolinyl acid has the structural formula (I) below:

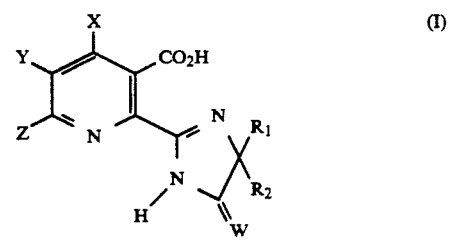

(I)

wherein
W is oxygen or sulfur;
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$-$C_6$ cycloalkyl optionally substituted with methyl;

X is hydrogen, halogen, hydroxyl or methyl;

Y and Z are independently hydrogen, halogen, $C_1$-$C_6$alkyl, $C_1$-$C_4$ alkoxyalkyl, hydroxloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino, or $C_1$-$C_4$ alkysulfonyl group or phenyl optionally substituted with one $C_1$-$C_4$ alkyl, $C_1$-$C_4$ alkoxy or halogen; and when taken together, Y and Z may form a ring in which YZ are represented by the structure: $-(CH_2)_n-$, where n is an integer of 3 or 4, provided that X is hydrogen; or

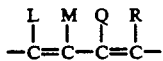

where L, M, Q and R are independently hydrogen, halogen, $C_1$-$C_4$alkyl or $C_1$-$C_4$alkoxy;

and the 2,6-dinitroaniline derivative has the structural formula (II) below:

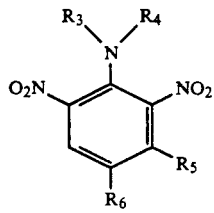

wherein $R_3$ is hydrogen, $C_2$-$C_4$alkyl or chloroethyl;

$R_4$ is $C_2$-$C_5$ alkyl, chloroethyl, 2-methallyl or cyclopropylmethyl;

$R_5$ is hydrogen, methyl or amino;

$R_6$ is trifluoromethyl, $C_1$-$C_3$alkyl, -$SO_2NH_2$ or $SO_2CH_3$.

2. The composition according to claim 1 comprising on a weight basis 2% to 6% of the ethylene oxide/propylene oxide block copolymer, 1% to 6% of the alkylphenol polyethylene oxide condensate, 0.5% to 10% of the antigelation agent and a sufficient amount of the aromatic solvent to total 100%.

3. The composition according to claim 2 wherein the alkylarylsulfonic acid is a $C_8$-$C_{18}$ benzenesulfonic acid, the ethylene oxide/propylene oxide block copolymer is a butyl-omega-hydroxy-poly(oxypropylene) block polymer with poly(oxyethylene), the alkylphenol polyethylene oxide condensate is a nonylphenol ethoxylate, the antigelation agent is N-methylpyrrolidone, cyclohexanone, an alcohol or a glycol and the aromatic solvent is an aromatic hydrocarbon mixture having a distillation range of from about 140° C. to 305° C.

4. The composition according to claim 3 wherein the $C_8$-$C_{18}$ alkylbenzenesulfonic acid is dodecylbenzenesulfonic acid, the butyl-omega-hydroxypoly(oxypropylene) block polymer with poly(oxyethylene) is alpha-butyl-omega-hydroxy-ethylene oxide-propylene oxide block copolymer having a HLB of 12 and a viscosity at 25° C. of 2,000 CPS, the nonylphenol ethoxylate is nonylphenol ethoxylate (9 to 10 mols of ethylene oxide), the antigelation agent is N-methylpyrrolidone, and the aromatic hydrocarbon mixture has a distillation range of from about 183°0 C. to 280° C.

5. The composition according to claim 3 wherein the imidazolinyl acid is selected from the group consisting of 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)nicotinic acid, 2-(4-isopropyl-4-methyl-5-oxo-2-imidazolin-2-yl)nicotinic acid and 2-(4-isopropyl-4-methyl-5-oxo-2-imidazolin-2-yl)-5-(methoxymethyl) nicotinic acid; and the 2,6-dinitroaniline derivative is selected from the group consisting of pendimethalin and trifluralin.

6. The composition according to claim 5 wherein the imidazolinyl acid is 5-ethyl-2-(4-isopropyl-4-methyl-5-oxo-2-imidazolin-2-yl)nicotinic acid and the 2,6-dinitroaniline derivative is pendimethalin.

7. The composition according to claim 5 wherein the imidazolinyl acid is 5-ethyl-2-(4-isopropyl-4-methyl-5-oxo-2-imidazolin-2-yl)nicotinic acid and the 2,6-dinitroaniline derivative is trifluralin.

* * * * *